(12) United States Patent
Geisler et al.

(10) Patent No.: US 8,798,233 B2
(45) Date of Patent: Aug. 5, 2014

(54) LOW DOSE-RATE RADIATION FOR MEDICAL AND VETERINARY THERAPIES

(75) Inventors: Fred Harden Geisler, Chicago, IL (US); Lois Ann Polatnick, Chicago, IL (US); Daniel N. Slatkin, Essex, CT (US)

(73) Assignee: Microbeam Therapy, LLC, Redwood City, CA (US)

( * ) Notice: Subject to any disclaimer, the term of this patent is extended or adjusted under 35 U.S.C. 154(b) by 297 days.

(21) Appl. No.: 13/369,368

(22) Filed: Feb. 9, 2012

(65) Prior Publication Data
US 2013/0208865 A1 Aug. 15, 2013

(51) Int. Cl.
*A61N 5/10* (2006.01)

(52) U.S. Cl.
USPC .................. 378/65; 378/147; 378/205

(58) Field of Classification Search
CPC ...... A61N 5/10; A61N 5/1001; A61N 5/1049; A61N 2005/1061; A61N 5/103; G21K 1/02; G21K 1/04; A61B 6/06; A61B 6/10; A61B 6/107
USPC ............. 378/65, 68, 147, 149, 150, 204, 205; 250/515.1
See application file for complete search history.

(56) References Cited

U.S. PATENT DOCUMENTS

| | | | |
|---|---|---|---|
| 4,010,373 A * | 3/1977 | Kay | .................. 250/453.11 |
| 5,339,347 A | 8/1994 | Slatkin et al. | |
| 5,771,270 A | 6/1998 | Archer | |
| 2006/0176997 A1 | 8/2006 | Dilmanian et al. | |

OTHER PUBLICATIONS

International Search Report in corresponding PCT Application No. PCT/US2013/025267, issued on Apr. 3, 2013.
Ahunbay et al, "Direct Aperture Optimization-Based Intensity-Modulated Radiotherapy for Whole Breast Irradiation", Int. J. Radiation Oncology Biol. Phys., vol. 67, No. 4, 2007, pp. 1248-1258.
Slatkin et al, "Prospects for Microbeam Radiation Therapy of Brain Tumours in Children", Medical Department Brookhaven National Laboratory, 2008, p. 163.
W.P.M. Mayles, "Survey of the Availability and Use of Advanced Radiotherapy Technology in the UK", Clinical Oncology 22 (2010) pp. 636-642.
Beilajew, "The Effect of Strong Longitudinal Magnetic Fields on Dose Deposition from Electron and Photon Beams", Med. Phys. 20 (4), Jul./Aug. 1993, pp. 1171-1179.
Keall et al, "Electromagnetic-Guided Dynamic Multileaf Collimator Tracking Enables Motion Management for Intensity-Modulated ARC Therapy", Int. J. Radiation Oncology Biol. Phys., vol. 79, No. 1, 2011, pp. 312-320.
E. Brauer-Krisch et al, "Characterization of a Tungsten/Gas Multislit Collimator for Microbeam Radiation Therapy at the Europeam Synchrotron Radiation Facility", Review of Scientific Instruments 76, 2005, 7 pages.

(Continued)

*Primary Examiner* — Jurie Yun
(74) *Attorney, Agent, or Firm* — Kramer Amado, P.C.

(57) ABSTRACT

Various embodiments relate to a method of performing microbeam radiation therapy on a subject, including: affixing a collimator to the subject at a first location; producing a first high energy radiation fan beam, wherein the width of the first fan beam in a first direction is greater than the width of the first fan beam in a second direction; and moving the subject in the second direction so that the first fan beam irradiates the subject through the collimator to produce first high dose regions alternating with first low dose regions.

11 Claims, 3 Drawing Sheets

(56) References Cited

OTHER PUBLICATIONS

E. Brauer-Krisch et al, "Effects of Pulsed, Spatially Fractionated, Microscopic Synchrotron X-Ray Beams on Normal and Tumoral Brain Tissue", Mutation Research 704/Reviews in Mutation Research, (2010), pp. 160-166.
E. Brauer-Krisch, "New Technology Enables High Precision Multislit Collimators for Microbeam Radiation Therapy", Review of Scientific Instruments 80, (2009), 6 pages.
Jian-Rong Dai et al, "Intensity-Modulation Radiotherapy Using Independent Collimators: An Algorithm Study", Med. Phys. 26 (12), 1999, pp. 2562-2570.
Hargrave et al, "Diffuse Brainstem Glioma in Children: Critical Review of Clinical Trials", http://oncology.thelancet.com, vol. 7, 2006, pp. 241-248.
Kalef-Ezra, "Health Physics Aspects in Treatment Rooms After 18-MV X-Ray Irradiations", Radiation Protection Dosimetry (2011), vol. 147, No. 1-2, pp. 1-6.
J.A. Laissue et al, "Prospects for Microbeam Radiation Therapy of Brain Tumours in Children to Reduce Neurological Sequelae", Developmental Medicine & Child Neurology, 2007, 49: 577-581.
Laissue et al, "The Weanling Piglet Cerebellum: A Surrogate for Tolerance to MRT (Microbeam Radiation Therapy) in Pediatric Neuro-Oncology", Proceedings of SPIE, vol. 4508 (2001), pp. 65-73.
Fan et al, "Intensity Modulation Under Geometrical Uncertainty: A Deconvolution Approach to Robust Fluence", Physics in Medicine and Biology 55 (2010), pp. 4029-4045.
Bert et al, "Motion 41 Radiotherapy: Particle Therapy", Physics in Medicine and Biology 56 (2011), pp. R113-R144.
Serduc et al, High-Precision Radiosurgical Dose Delivery by Interlaced Microbeam Arrays of High-Flux Low-Energy Synchrotron X-Rays, Synchrotron X-Ray Radiosurgery, vol. 5, issue 2, 2010, pp. 1-12.
Slatkin, "Uniaxial and Biaxial Irradiation Protocols for Microbeam Radiation Therapy", Institute of Physics Publishing, Phys. Med. Biol. 49 (2004), pp. N203-N204.
Slatkin, "Tetrahedral Irradiation Protocol for Microbeam Radiation Therapy", Institute of Physics Publishing, Phys. Med. Biol. 51 (2006), pp. N295-N297.
Cai et al, "Targeted Cancer Therapy with Tumor Necrosis Factor-Alpha", Biochemistry Insights, 2008, pp. 5-21.
Gonsalves et al, "Tunable Laser Plasma Accelerator Based on Longitudinal Density Tailoring", Nature Physics, 2011, pp. 1-5.
Esteban et al, "Reducing the Number of Segments in Unidirectional Segmentations of Fluence Matrices for Multileaf Collimators in IMRT", M.Sc. Biomedical Engineering, 2010, pp. i-xii and 1-30.

* cited by examiner

LOW DOSE-RATE RADIATION FOR MEDICAL AND VETERINARY THERAPIES

TECHNICAL FIELD

Various exemplary embodiments disclosed herein relate generally to low dose-rate radiation for medical and veterinary therapies. Such application is especially useful in treating various cancers and other tumors.

BACKGROUND

Cancer continues to be one of the foremost health problems. Conventional treatments such as surgery and chemotherapy have been extremely successful in certain cases; in other instances, much less so. Radiation therapy has also exhibited favorable results in many cases, while failing to be completely satisfactory and effective in all instances. An alternative form of radiation therapy, known as microbeam radiation therapy (MRT) may be used to treat certain tumors for which the conventional methods have been ineffective.

MRT differs from conventional radiation therapy by employing multiple parallel fan beams of radiation with a narrow dimension or thickness that may be on the order of 10 um to 200 um. The thickness of the microbeams is dependent upon the capacity of tissue surrounding a beam path to support the recovery of the tissue injured by the beam. It has been found that certain types of cells, notably endothelial cells lining blood vessels, have the capacity to migrate over microscopic distances, infiltrating tissue damaged by radiation and reducing tissue necrosis in the beam path. In MRT, sufficient unirradiated or minimally irradiated microscopic zones remain in the normal tissue, through which the microbeams pass, to allow efficient repair of irradiation-damaged tissue. As a result, MRT is fundamentally different from other forms of radiation therapy.

In conventional forms of radiation therapy, including the radiosurgical techniques employing multiple convergent beams of gamma radiation, each beam is at least several millimeters in diameter, so that the biological advantage of rapid repair by migrating or proliferating endothelial cells is minimal or nonexistent. Observations of the regeneration of blood vessels following MRT indicate that endothelial cells cannot efficiently regenerate damaged blood vessels over distances on the order of thousands of micrometers (μm). Thus, in view of this knowledge concerning radiation pathology of normal blood vessels, the skilled artisan may select a microbeam thickness as small as 10 μm to 200 μm. Further, the microbeams may include substantially parallel, non-overlapping, planar beams with center-to-center spacing of from about 50 μm to about 500 μm. Also, the beam energies may range from about 30 to several hundred keV. These microbeams result in a dosage profile with peaks and valleys. The radiation dosage in the peaks is large enough to kill the targeted tumor, but also kills healthy cells in the peak dosage areas. The radiation dosage in the valleys is small enough to prevent any damage to cells in the valley dosage areas.

A division of a radiation beam into microbeams and the use of a patient exposure plan that provides non-overlapping beams in the tissue surrounding the target tumor allows the non-target tissue to recover from the radiation injury by migration of regenerating endothelial cells of the small blood vessels to the areas in which the endothelial cells have been injured beyond recovery. Therefore, the probability of radiation-induced coagulative necrosis in normal, non-targeted tissue is lowered, which may improve the effectiveness of clinical radiation therapy for deep-seated tumors. The use of microbeams may be of special benefit for deep tumors.

Various studies have shown the microbeam tissue-sparing effect for X-ray microbeams. Although other methods and processes are known for radiation therapy, none provides a method for performing radiation therapy while avoiding significant radiation-induced damage to tissues surrounding the target.

Present radiation therapies often take many days and weeks of treatment to provide enough radiation to a target tumor. On the other hand, MRT can provide an effectual treatment in single visit. Very high energy radiation may be used with MRT that results in the destruction of tumor tissue while allowing for the regeneration of healthy tissue affected by the microbeam fan beams.

Further, MRT provides a method for treating cancerous tumors by using extremely small radiation microbeams increasing the precision and accuracy of radiation therapy. MRT also provides a method of using extremely small microbeams of radiation to unexpectedly produce effective radiation therapy while avoiding significant radiation-induced damage to non-target tissues.

A major benefit of MRT is that the microbeams are so narrow that the vasculature of the tissue through which the microbeams pass can repair itself by the infiltration of endothelial cells from surrounding unirradiated tissue. Present knowledge indicates that such infiltration can take place only over distances on the order of less than 500 μm depending on the tissue being irradiated. The dimensions of the microbeams and the configuration of the microbeam array are therefore determinable with reference to the susceptibility of the target tissue and the surrounding tissue to irradiation and the capacities of the various involved tissues to regenerate.

U.S. Pat. No. 5,339,247 to Slatkin et al. entitled Method for Microbeam Radiation Therapy provides background related to MRT, and is hereby incorporated by reference for all purposes.

SUMMARY

Accordingly, there is a need for improved radiation therapies that can quickly yet safely treat patients. Further there is a need to focus radiation doses in desired peak dosage regions will minimizing radiation doses in desired valley dosage regions.

A brief summary of various exemplary embodiments is presented. Some simplifications and omissions may be made in the following summary, which is intended to highlight and introduce some aspects of the various exemplary embodiments, but not to limit the scope of the invention. Detailed descriptions of a preferred exemplary embodiment adequate to allow those of ordinary skill in the art to make and use the inventive concepts will follow in the later sections.

Various embodiments may also relate to a method of performing microbeam radiation therapy on a subject, including: affixing a collimator to the subject at a first location; producing a first high energy radiation fan beam, wherein the width of the first fan beam in a first direction is greater than the width of the first fan beam in a second direction; and moving the subject in the second direction so that the first fan beam irradiates the subject through the collimator to produce first high dose regions alternating with first low dose regions.

BRIEF DESCRIPTION OF THE DRAWINGS

In order to better understand various exemplary embodiments, reference is made to the accompanying drawings wherein.

DETAILED DESCRIPTION

Figure 1:
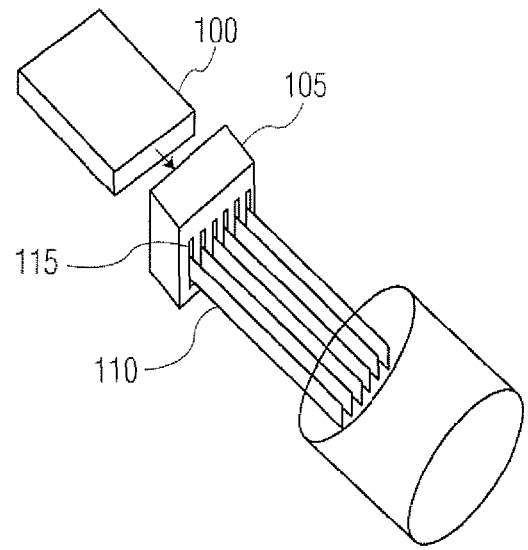
FIG. 1 illustrates a method for producing microbeams using a collimator.

Referring now to the drawings, in which like numerals refer to like components or steps, there are disclosed broad aspects of various exemplary embodiments.

FIG. 1 illustrates a method for producing microbeams using a collimator. The collimator 105 may include a plurality of parallel slits 115 in a vertical direction. A high energy radiation fan beam 100 that may be very narrow in the vertical direction and wide in the horizontal direction may pass through the collimator 105. Because the collimator 105 is made of a high Z material, it blocks portions of the of the high energy radiation fan beam 100. The portion of the high energy radiation fan beam 100 that passes through the slits 115 of the collimator 105 forms the microbeams 110. The microbeams 110 may be used to treat a subject. Depending upon the vertical height of the fan beam 100 relative to the size of the treatment region, the subject may have to be moved relative to the microbeams 110 in order to irradiate the whole treatment region. It is not possible to move the high energy radiation fan beam 100 because of the massive size of the facility necessary to produce the high energy radiation fan beam 100. Further, the collimator 105 has been fixed relative to the high energy fan beam 100.

MRT may apply very high energy radiation beams for a very short period of time. One problem with MRT may occur when the subject moves relative to the beam during treatment. This may result in smearing of the peak and valley doses applied to the subject. Effective and safe MRT relies upon valley dose regions where the radiation dose is low enough to prevent any damage to the healthy cells in the valley dose regions. If the subject moves relative to the microbeams 110 during treatment, then the high energy radiation of the microbeams 110 may smear into the valley dose regions resulting in many if not all of the healthy cells along the path of the microbeams 110 being injured beyond recovery. Accordingly there is a need to stabilize and fix the microbeams 110 relative to the subject.

The microbeams 110 may be fixed relative to the subject by affixing a collimator to the subject that splits a high energy fan beam 100 into microbeams 110. In this embodiment, even though the subject may move relative to the high energy fan beam 100, the collimator moves with the subject, hence the microbeams 115 emanating from the collimator move with the subject as well. This embodiment may prevent the problem described above.

Figure 2:
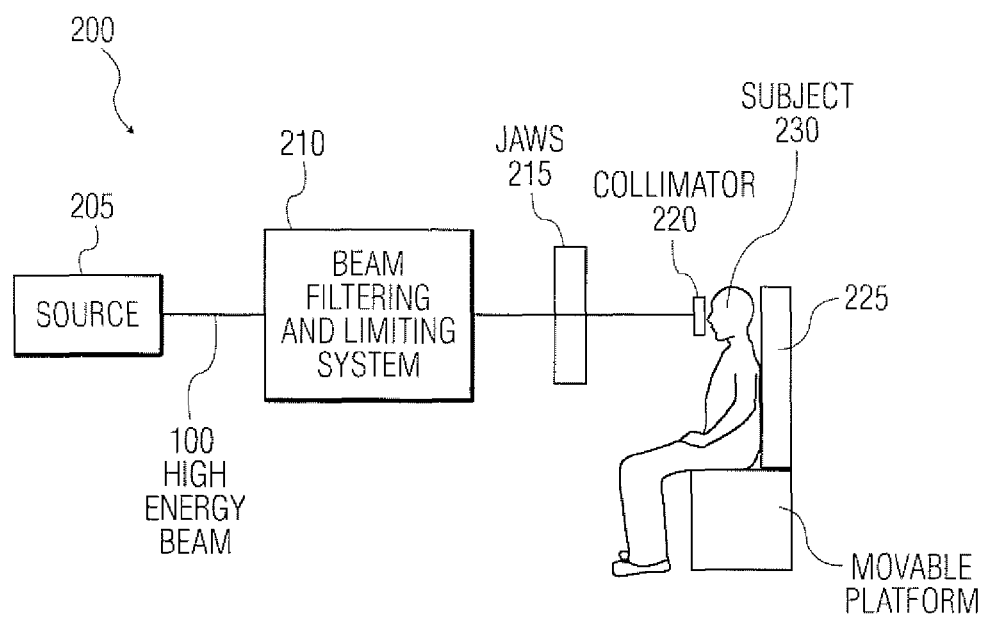
FIG. 2 illustrates an embodiment of a MRT system.

FIG. 2 illustrates an embodiment of a MRT system. The MRT system 200 may include a source 205 that produces a high energy fan beam 100, a beam filtering and limiting system 210, jaws 215, a collimator 220, and a movable platform 225. A subject 230 may be treated by the MRT system 200.

The source 200 may produce high energy electromagnetic radiation beam such as X-ran or gamma radiation beam. High energy X-ray radiation may be especially beneficial. In any generated photon beam, the photons are produced having a characteristic spectrum of energies. The photon energy of the beams may range of from about 30 keV to about 300 keV.

A synchrotron may be used to generate an X-ray beam having practically no divergence and a very high fluence rate. These synchrotron generated X-rays have the potential for projecting sharply defined beam edges deep in the body. This source may be useful for generating X-ray microbeams for radiobiology, radiotherapy, and radiosurgery. A high fluence rate is required to implement MRT because exposure times must be short enough (e.g., less than about 1 second) to avoid the blurring of margins of the irradiated zones of tissue due to body or organ movements. Sharply defined microbeam margins are made possible not only by the high fluence rate and the minimal divergence of the synchrotron beam, but also by the microscopically short ranges in tissue of secondary electrons generated by 50-150 keV synchrotron X-rays. Absorbed doses to nontargeted tissues situated between microbeams may be kept below the threshold for radiation damage in tissues both proximal and distal to the isocentric target, i.e., where the microbeams do not overlap. These factors make it possible to effectively irradiate a target using a field of many well defined, closely spaced microbeams.

The radiation beam for producing the microbeam array may be obtained from industrial X-ray generators or from synchrotron beamlines at electron storage rings. The radiation beam may be obtained from a wiggler beam line at an electron storage ring. A conventional "planar" wiggler uses periodic transverse magnetic fields to produce a beam with a rectangular cross-section, typically having a horizontal to vertical beam opening angle ratio on the order of 50:1. In an alternative embodiment, the radiation beam is obtained from a "helical" wiggler, a configuration capable of producing a substantially less anisotropic beam. While a fan beam is discussed in the embodiment below, it is also possible to place the subject to be treated a large distance (i.e., >100 m) from the source 200, which may allow the X-ray beam from the source to expand enough in both the horizontal and vertical directions so that the beam covers the whole treatment region, and hence, it may not be necessary to move the subject relative to the high energy beam. Further, such beam spreading could be accomplished by two orthogonal wigglers that would spread the beam first in one direction and then in a second orthogonal direction. Such embodiments would not require movement of the subject, but the collimator would still be affixed to the subject as with the previously described embodiments.

The beam filtering and limiting system 210 filters and limits the high energy beam 100 for treating the subject 230. As mentioned above the source may produce a high energy beam with a range of energies. Often only a certain range of energies may be used to treat the subject. Accordingly, various filters made of various materials may be placed in the path of the high energy beam to filter out the undesired energy bands in the high energy beam. Further, spatial limiting may be used to limit the beam to the desired beam size and geometry. This may help to prevent unwanted and unsafe stray radiation from the source 200. Such spatial limiting may be accomplished, for example, with plates having slits. The plates may be of sufficient thickness and high Z material to block portions of the high energy beam from the source 200.

Jaws 215 further spatially limit the high energy beam 100 that has passed though the filtering and limiting system 210. The jaws 215 include two jaws that may be made of a material that completely blocks the high energy beam 100. Because the width of the high energy fan beam typically may be wider than the target region, it may be necessary to limit the width of the fan beam to the width of the target region. Thus, as the subject 230 moves relative to the high energy fan beam 100, the width of the target region varies. Accordingly, the jaws 215 move to adjust the width of the high energy fan beam 100 to correspond to the width of the target region being irradiated by the high energy fan beam 100. Prior to the subject being treated using MRT, the target region is very accurately measured, so that during treatment with the high energy fan beam 100, the width of the beam can be adjusted to correspond the precise desired treatment region. This may prevent the unnecessary irradiation of normal healthy tissue adjacent to the treatment region.

The two jaws 215 may be independently controlled so as to adjust the location of edges of the high energy fan beam 100 so that the edges coincide with the edges of the treatment region. Further, actuators that move the jaws 215 may be able to move the jaws 215 quickly enough to adjust the width of the high energy fan beam 100. The movement of the jaws may be controlled by a controller that receives information relating to the shape and location of the treatment region. Further, the controller may include a processor for controlling the movement of the jaws 215. Further, while the jaws 215 are shown as spatially independent from the collimator 220, it is also possible that the jaws 215 may be connected to the collimator or the patient so that it moves with the patient as well.

The width adjusted high energy fan beam 100 may irradiate the collimator 220. As described above with respect to the FIG. 1, the collimator 220 may include a plurality of vertical slits. The vertical slits split the high energy fan beam 100 into a plurality of microbeams 110 (as shown in FIG. 1). The collimator 220 may be affixed securely to the subject. Preferably, the collimator 220 is very near the subject 230 or even in contact with the skin of the subject 230. As a result, the micro beams formed by the collimator 220 are fixed relative to the subject, even if the subject moves.

Figure 3:
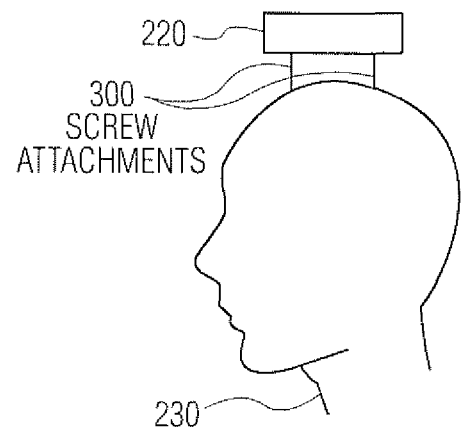
FIG. 3 illustrates affixing a collimator to the skeleton of a subject.

The collimator 220 may be fixed to the skeleton of the subject 220 as shown in FIG. 3. The collimator 220 may be attached to the subject 230 using screws 300 or another fastener 300 that may be used to affix items to the skeleton. The collimator may be affixed to the skull as shown in FIG. 3, but may also be affixed, for example, to the skull, the hip, the spine, the clavicle, or to bones in the arm or the leg.

Figure 4:
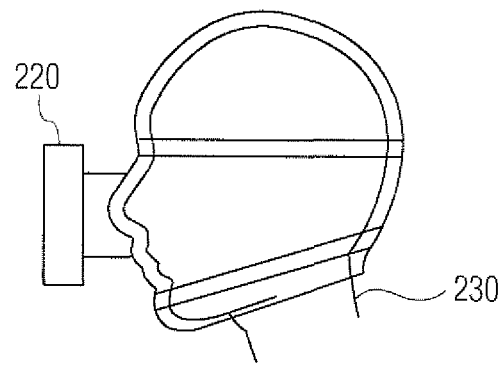
FIG. 4 illustrates affixing a collimator to a subject using a facial mask.

The collimator 220 may also be affixed to the subject 230 using a facial mask 400 as shown in FIG. 4. A facial mask 400 may be placed over the face of the subject 230 and held in place using straps or any other secure method. Then the collimator 220 may be attached to the mask 400.

Further, the collimator 220 may be affixed to the subject 230 by clamping the collimator 220 or a related fixture between the upper and lower jaws of the subject. The subject's jaws may then be held in place using straps or some other method.

Also, a fixture may be used to help affix the collimator 220 to the subject 230. The fixture may be attached to the face, skeleton, jaw or other stable part of the subject. Then the collimator 220 may be attached to the fixture.

It is important to precisely and accurately affix the collimator 220 relative to the target region in the subject 230 that is to be treated. This may be accomplished by affixing the collimator or the fixture to the subject 230 in the desired location. Then a diagnostic test may be performed to verify the alignment of the collimator 230 or fixture with the treatment region. Then the location of the collimator 230 or the fixture may be adjusted, and the diagnostic test repeated. This process may be repeated as many times as needed to achieve the desired alignment accuracy between the collimator 220 and the target region of the subject 230.

The movable platform 225 may hold the subject in a fixed position and then move the subject relative to the high energy fan beam 100. The movable platform 225 may be any known platform that secures the patient and then allows for very precise movement of the patient relative to the high energy fan beam 100.

Further, the MRT may be conducted in order to accommodate tissue movement in the subject due to the cardiac or respiratory cycle. The on-time of the high energy beam 100 may be synchronized with either the cardiac or the respiratory cycle or both. Each on-time may be limited to a small time interval during the appropriate cycle to avoid the smearing of the extraordinarily precise microbeam effect by movement of the tissue generated by cardiogenic and respiratory pulsation. For example, the on-time of the high energy beam 100 may be limited to the end phase of diastole or the end phase of an exhalation cycle. Other predicable points of these cycles may be used as well. In yet another embodiment, the diagnostic tests performed to characterize the target region or to align the collimator with the target region may be carried out at specific predetermined portion of the cardiac or respiratory cycle. Then the on-time of the high energy beam 100 may be during the same specific predetermined portion of the cardiac or respiratory cycle, and may include one or more on-time periods. The use of compensation for the cardiac and respiratory cycle may depend on the target regions susceptibility to movement due to these cycles.

Because such high energy radiation may be used in MRT it is very important to precisely control the dose of radiation applied to the subject 230. Prior to treatment, a medical physicist may use sophisticated computer tools and modeling to determine the dosage parameters to use during the MRT. In order to evaluate the MRT dosage, a film containing an array of microscopic cell-culture chambers may be used. The film may be placed downstream from the collimator 220 in close proximity to or in contact with the subject's skin. Those cells behind the radiolucent slits and their similar but minimally irradiated cells in the same film behind the radio-opaque bars of the collimator between its radiolucent slits would indicate, with nearly cell-by-cell spatial resolution, the biologically effective dose received by the skin cells, which are important reference doses for computation by the medical physicist of valley doses in radiosensitive vital normal tissues deep to the skin, proximal and distal to the target region, outlined in diagnostic tests. Such a film may also be placed near the collimator 220 without a subject and irradiated to determine the biological effects of a proposed treatment dosage.

While the application of a single MRT dose may be effective to effectively treat a subject, it may also be beneficial to provide multiple treatments from different directions. The treatment directions and doses would be selected to allow the two different sets of microbeams to intersect in the target region. These multiple doses of high energy radiation to the treatment region may increase the effectiveness of the MRT.

While the high radiation beam 100 is described as being spread in the horizontal direction, it may be beneficial to spread the beam in the vertical direction or any other direction. Using other beam spreading directions may provide benefits in accurately delivering a dose. Also, if multiple MRT treatments are used, then the ability to spread the high energy beam 100 in various directions may be beneficial. For example, when producing high energy X-rays using a synchrotron, a wiggler may be used to spread the beam in a desired direction. Such a wiggler may be mounted so that it can be rotated around an axis parallel to the high energy beam. As a result the beam may be spread in any desired direction. The rotation of the wiggler may be precisely and accurately controlled to allow the beam to spread as needed to apply the desired radiation dose.

Prior research has shown that blanching the subject's skin during the application of MRT, reduces the damage done to skin cells by MRT. Accordingly, this benefit may be combined with the treatment method and system according the present embodiments. Blanching of the skin may be accomplished by applying pressure to the skin irradiated by the microbeams 110. Such pressure may be applied by a tightly applying a bandage or bands to the skin. Further, pressure may be applied to the skin by using a bladder placed between the skin of the subject and the collimator 220. Another method of blanching the skin includes injecting adrenaline into an area near the skin to be blanched. Any other method of blanching the skin may be used as well.

Figure 5:
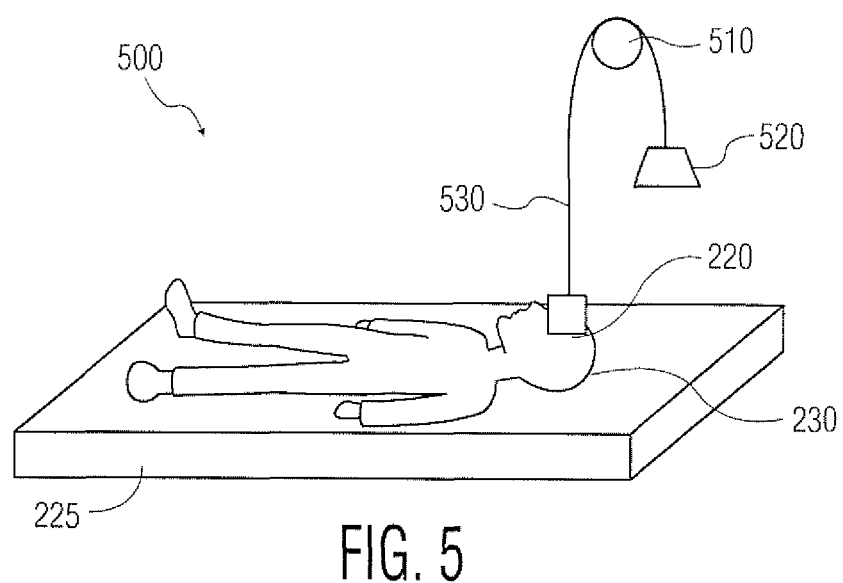
FIG. 5 illustrates a pulley system that may help to counter the weight of the collimator.

Because the collimator 220 may be heavy because of its size and the use of dense materials needed to block the high energy radiation beam 200, it may be uncomfortable to the subject to support the weight of the collimator 220. Accordingly, this weight may be offset using a pulley or lever arm system. FIG. 5 illustrates a pulley system 500 that may help to counter the weight of the collimator 230. The pulley system 500 may include a pulley 510, a counter-weight 520, and a cable 530. The cable 530 may attach to the collimator 220 and then extend through and over pulley 510 and then attach to the counter-weight 520. The counter-weight 520 is approximately the same weight as the collimator 220, so that the effective weight of the collimator 220 on the subject is nearly zero. Further, the pulley may be subject to a small frictional force to minimize the movement of the pulley except when a sufficient force is applied to the cable 530.

Figure 6:
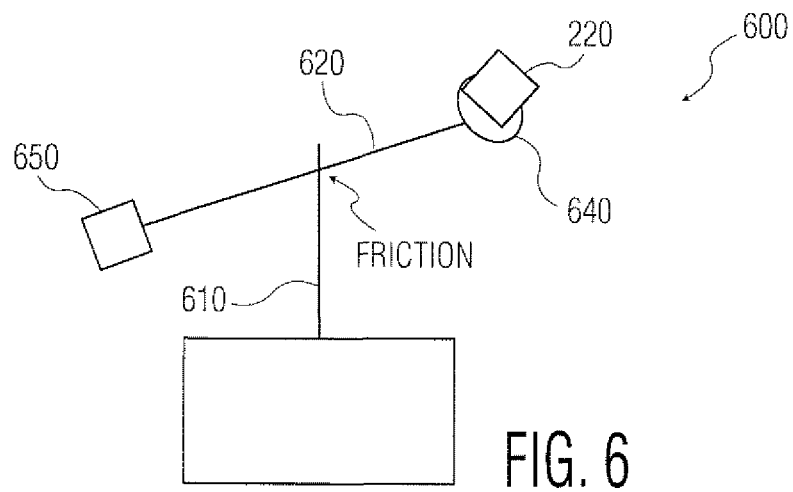
FIG. 6 illustrates another embodiment of a system to counter the weight of the collimator.

FIG. 6 illustrates another embodiment of a system 600 to counter the weight of the collimator 230. The lever system 600 may include a base 610, a lever arm 620, a counter-weight 630, and gimbal 640. The base 610 supports the lever arm 620 and allows the lever arm 620 to pivot about a connection point between the base 610 and the lever arm 620. A counter-weight 630 is attached to one end of the lever arm 630 to counterbalance weight at the gimbal end of the lever arm 630. The weight of the counter-weight 630 may be selected in order to counter the weight of the collimator 220. The collimator 220 may be attached to a gimbal 640 at the end of the lever arm 620 opposite the counter-weight 630. The gimbal allows the collimator 220 be oriented in any needed direction. Other mechanical systems may be used as well to offset the weight of the collimator 220 in order to prevent discomfort to the subject.

As described above with respect to FIG. 1, the collimator 105 may include alternating radiation translucent regions and radiation opaque regions. The radiation translucent regions may be slits 115 formed in a radiation opaque material. Also, the radiation translucent region may be made of a radiation translucent material that allows the high energy beam 100 to pass through the collimator 105 to form the microbeams 110.

Figure 7:
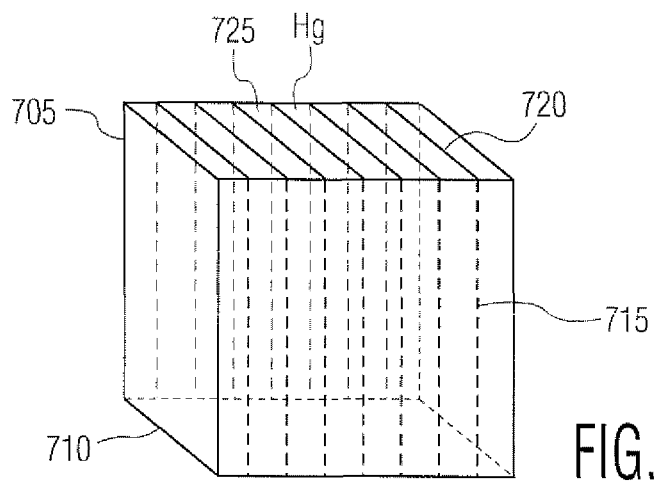
FIG. 7 illustrates one embodiment of a collimator.

FIG. 7 illustrates one embodiment of a collimator. The collimator 705 may include an enclosure 710, radiation translucent foils 720, and radiation opaque liquid 725. The enclosure 710 may have two substantially parallel opposite sides with grooves 715. The radiation translucent foils 720 may be mounted in opposite pairs of grooves 715. All of the radiation translucent foils 720 may be substantially parallel to one another. The radiation translucent foils 720 may be made of aluminum or any other material that is sufficiently radiation translucent. Next a liquid radiation opaque material such as mercury maybe added to the regions in between the radiation translucent foils 720. Such a collimator 705 would allow for the easy construction of various collimators 705 with various parameters, such as foil height, width, and thickness and the spacing between the foils.

Figure 8:
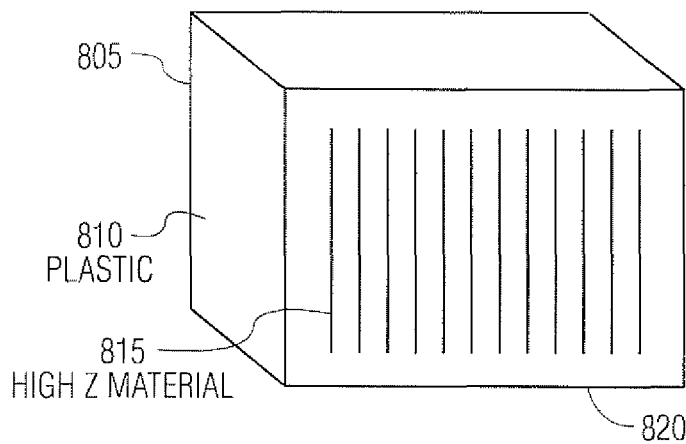
FIG. 8 illustrates another embodiment of a collimator.

FIG. 8 illustrates another embodiment of a collimator. The collimator 805 may include a body 810 and layers 815. The body may be made of a radiation translucent material such as for example plastic. Plastic has the advantage that it may be easily machined to create slits. The slits may be formed using micromachining techniques. Further, the body 810 may include a machinable side 820. This machinable side may be machined to conform to specific portion of the subject's body. This would allow for accurate, stable, and comfortable placement of the collimator 805 in contact with the subject.

Although the various exemplary embodiments have been described in detail with particular reference to certain exemplary aspects thereof, it should be understood that the invention is capable of other embodiments and its details are capable of modifications in various obvious respects. As is readily apparent to those skilled in the art, variations and modifications can be affected while remaining within the spirit and scope of the invention. Accordingly, the foregoing disclosure, description, and figures are for illustrative purposes only and do not in any way limit the invention, which is defined only by the claims.

We claim:

1. A microbeam radiation therapy system receiving a high energy radiation fan beam, comprising:
    a collimator with slits, wherein the collimator only passes the high energy radiation fan beam through the slits;
    a fixture attached to the collimator, wherein the fixture is configured to be attached to a subject; and
    a set of adjustable jaws configured to block a portion of the high energy radiation beam.

2. The system of claim 1, wherein the slits are filled with a radiation translucent material.

3. The system of claim 1, wherein the fixture includes a mask configured to be attached to a face of the subject.

4. The system of claim 1, further comprising:
    a pulley;
    a weight;
    a cable attached to the weight and the collimator with the pulley in between.

5. The system of claim 1, further comprising:
    a base;
    a lever arm attached to the base;
    a weight attached to a first end of the lever arm; and
    a gimbal attached to a second end of the lever arm and attached to the collimator.

6. The system of claim 1, further comprising a controller that controls a width of the adjustable jaws, where the width corresponds to a width of a desired treatment region.

7. The system of claim 1, further comprising a movable platform configured to securely hold the subject.

8. The system of claim 1, further comprising a source that produces the high energy radiation fan beam.

9. The system of claim 8, wherein the source is a synchrotron.

10. The system of claim 8, wherein the source includes a rotatable wiggle that changes the orientation of the high energy radiation fan beam.

11. The system of claim 10, wherein the source is a synchrotron.

* * * * *